United States Patent [19]

Nysted

[11] Patent Number: 4,495,102

[45] Date of Patent: Jan. 22, 1985

[54] AMINOALKYL STEROIDS

[75] Inventor: Leonard N. Nysted, Highland Park, Ill.

[73] Assignee: G. D. Searle & Co., Skokie, Ill.

[21] Appl. No.: 414,717

[22] Filed: Sep. 3, 1982

[51] Int. Cl.³ .............................................. C07J 43/00
[52] U.S. Cl. ..................... 260/239.5; 260/239.55 C;
260/397.3; 260/397.2; 260/239.57
[58] Field of Search ............... 260/239.5, 397.4, 397.2,
260/239.55 C, 397.3, 397.1, 239.57

[56] References Cited

U.S. PATENT DOCUMENTS

| 4,191,759 | 3/1980 | Johnston et al. | 260/239.5 |
| 4,289,762 | 9/1981 | Metcalf et al. | 260/397.4 |
| 4,298,538 | 11/1981 | Neef et al. | 260/397.4 |

Primary Examiner—Elbert L. Roberts
Attorney, Agent, or Firm—Stuart L. Melton

[57] ABSTRACT

Compounds of Formula I and II are useful as potent antiarrythmic agents without significant effect on cardiac output and blood pressure.

49 Claims, No Drawings

AMINOALKYL STEROIDS

BACKGROUND OF THE INVENTION (a) Field of Invention

The present invention relates to certain novel aminosteroids. In particular, it relates to novel aminoalkyl steroids of Formula I and II which exhibit potent antiarrythmic and local anesthetic activity without significant effect on cardiac output and blood pressure.

Several drugs, which may be administered singly or in combination, are available for the treatment of cardiac rhythm disturbances. Proper management of cardiac arrhythmias begins with a precise electrocardiographic diagnosis of the arrhythmia at hand. Equally important is knowledge of the clinical setting in which the rhythm disturbance is occurring. The effectiveness will be enhanced if the physician has knowledge of the following aspects of a given drug: (1) site(s) of action, (2) dosage, route and rate of administration, (3) site of metabolism and route of excretion, (4) range of therapeutic plasma concentration, and (5) clinical and electrocardiographic manifestation of side effects of toxicity.

Lidocaine is used for the treatment of ventricular extrasystoles and ventricular tachycardia, but is ineffective in the treatment of atrial arrhythmias. Toxicity is not uncommon. The electrophysiologic properties of quinidine, disopyramide phosphate and procainamide are similar. Quinidine appears more effective than procainamide against atrial arrhythmias but is equally effective in the treatment of unifocal and multifocal ventricular extrasystoles and ventricular tachcardia. A problem with these agents, however, is the lowering effect in blood pressure and cardiac output that they have. Patients with low blood pressure must be carefully monitored to prevent complications. Cecil, Textbook of Medicine, 15th ed. pg. 1264–1266 (1979).

(b) Description of the Prior Art

A number of antiarrhythmic agents are currently known as described above. While a wide variety of steroids is also known, the novel compounds of the instant invention appear to have no close related art.

SUMMARY OF THE INVENTION

It has been discovered, therefore, that the following compounds are useful antiarrhythmics which do not show a decrease in cardiac output and blood pressure. A compound of the formula:

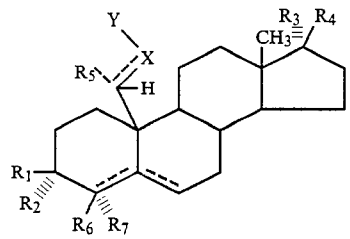

I wherein $R_1$ and $R_2$, each being the same or different, are:
(a) hydrogen;
(b) benzyloxy;
(c) hydroxyl;
(d) alkanoyloxy of from 1 to 6 carbon atoms, inclusive;
(e) wherein $R_1$ and $R_2$ are taken together to form a keto group; or
(f) wherein $R_1$ and $R_2$ are taken together to form a saturated or unsaturated heterocyclic ring of 5 or 6 members, which contains either:
(1) 2 oxygen atoms;
(2) 2 sulfur atoms; or
(3) 1 oxygen and 1 sulfur atom; the balance of the remaining ring atoms being carbon;

wherein $R_3$ and $R_4$, each being the same or different, are:
(a) hydrogen;
(b) alkyl from 1 to 10 carbon atoms, inclusive;
(c) alkanoyloxy of from 1 to 6 carbon atoms, inclusive;
(d) aralkyoxy;
(e) hydroxy;
(f) wherein $R_3$ and $R_4$ are taken together to form:
(1) a keto group;

(2)

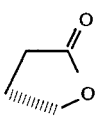

(g) wherein $R_3$ and $R_4$ are taken together to form a saturated or unsaturated heterocyclic ring or 5 or 6 members which contain either:
(1) 2 oxygen atoms;
(2) 2 sulfur atoms; or
(3) 1 oxygen and 1 sulfur atom; the balance of the ring atoms being carbon;
(h) wherein one of $R_3$ or 4 is of the formula:

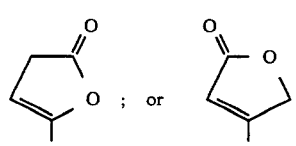

with the proviso that the remaining $R_3$ or $R_4$ is hydrogen;
(i)—$COOR_8$; or
(j) carboxyalkyl of from 2 to 5 carbon atoms, inclusive;
wherein $R_8$ is:
(a) hydrogen; or
(b) alkyl of from 1 to 6 carbon atoms, inclusive;
wherein $R_5$ is:
(a) hydrogen;
(b) hydroxyl; or
(c) trialkylsilyloxy;
with the proviso that $R_5$ is present only when the carbon to which it is attached is saturated;
wherein $R_6$ and $R_7$, each being the same or different, are:
(a) hydrogen; or
(b) alkyl of from 1 to 6 carbon atoms, inclusive, with the proviso that only one of $R_6$ or $R_7$ may be present when a 4,5 ring double bond exists;
wherein X is:
(a) alkyl of from from 1 to 6 carbon atoms, inclusive; or
(b) alkylidene of from 1 to 6 carbon atoms, inclusive, with the proviso that when X is alkylidene $R_5$ is not present;

wherein Y is:
 (a) —NR$_9$R$_{10}$; or
 (b) —N$^{(+)}$R$_{11}$R$_{12}$R$_{13}$ Z$^{(-)}$;
wherein R$_9$ and R$_{10}$, each being the same or different, are:
 (a) hydrogen;
 (b) alkyl of from 1 to 6 carbon atoms, inclusive;
 (c) alkanoyl of from 1 to 6 carbon atoms, inclusive;
 (d) aryl; or
 (f) aralkyl;
wherein R$_{11}$, R$_{12}$ and R$_{13}$, each being the same or different are:
 (a) alkyl of from 1 to 6 carbon atoms, inclusive;
 (b) aryl; or
 (c) aralkyl;
wherein Z is a pharmacologically acceptable negative ion; or the pharmacologically acceptable salts; the compounds of the invention being either hydrated of unhydrated. A compound of the formula:

wherein R$_1$ and R$_2$, each being the same or different, are:
 (a) hydrogen;
 (b) benzyloxy;
 (c) hydroxyl;
 (d) alkanoyloxy of from 1 to 6 carbon atoms, inclusive;
 (e) wherein R$_1$ and R$_2$ are taken together to form a keto group; or
 (f) wherein R$_1$ and R$_2$ are taken together to form a saturated or unsaturated heterocyclic ring of 5 or 6 members, which contains either:
   (1) 2 oxygen atoms;
   (2) 2 sulfur atoms; or
   (3) 1 oxygen and 1 sulfur atom; the balance of the remaining ring atoms being carbon;
wherein R$_3$ and R$_4$, each being the same or different are:
 (a) hydrogen;
 (b) alkyl of from 1 to 10 carbon atoms, inclusive;
 (c) alkanoyloxy of from 1 to 6 carbon atoms, inclusive;
 (d) aralkyl;
 (e) hydroxy;
 (f) wherein R$_3$ and R$_4$ are taken together to form:
   (1) a keto group; or
   (2)

(g) wherein R$_3$ and R$_4$ are taken together to form a saturated or unsaturated heterocyclic ring of 5 or 6 members which contain either:
   (1) 2 oxygen atoms;
   (2) 2 sulfur atoms; or
   (3) 1 oxygen and 1 sulfur atom; the balance of the ring atoms being carbon;
 (h) wherein one of R$_3$ or R$_4$ is of the formula:

with the proviso that the remaining R$_3$ or R$_4$ is hydrogen;
 (i) —COOR$_8$; or
 (j) carboxyalkyl of from 2 to 5 carbon atoms, inclusive;
wherein R$_8$ is:
 (a) hydrogen; or
 (b) alkyl of from 1 to 6 carbon atoms, inclusive;
wherein R$_5$ is:
 (a) hydrogen;
 (b) hydroxyl; or
 (c) trialkylsilyloxy;
wherein R$_6$ and R$_7$, each being the same or different, are:
 (a) hydrogen; or
 (b) alkyl of from 1 to 6 carbon atoms, inclusive with the proviso that only one of R$_6$ or R$_7$ may be present when a 4,5 ring double bond exists;
wherein T is —(CH$_2$)$_n$—; wherein n is an integer of from 1 to 2;
wherein R$_{14}$ is:
 (a) hydrogen
 (b) alkyl of from 1 to 6 carbon atoms; or
 (c) alkanoyl of from 1 to 6 carbon atoms, inclusive;

Examples of alkyl of from 1 to 6 carbon atoms are methyl, ethyl, propyl, butyl, pentyl, hexyl and the isomeric forms thereof.

Examples of alkanoyl of from 1 to 6 carbon atoms, inclusive are methanoyl, ethanoyl, propanoyl, butanoyl, pentanoyl, hexanoyl and the isomeric forms thereof.

Examples of aralkyl are benzyl, phenethyl, phenylpropyl and the isomeric forms thereof.

Examples of pharmacologically acceptable negative ions are iodide, bromide, chloride, sulfate, phosphate, acetate, propionate, lactate, maleate, malate, succinate, tartrate, ion exchange resins, and the like.

Antarrythmic activity was confirmed using isolated, aconitine-induced ventricular arrhythmia's in rabbits. The heart is isolated from adult albino rabbits of either sex that have recently been sacrificed. Ventricular tachycardia is induced to a level at least double the normal heart rate by injecting 0.05 ml of 0.1% aconitine nitrate into the apex of each of 2 rabbit hearts. The test compound is added in units sufficient to produce cumulative bath concentrations of 10, 20 and 40 mg/L. A compound is considered active if any concentration up to 40 mg/L produces a 50% or greater reduction in the ventricular rate in half or more of the tests performed. Drugs may slow the arrhythmia by prolonging the diastolic depolarization of the ectopic pacemaker, prolonging refractory period or increasing diastolic threshold. Quinidine, procainamide and diphenylhydantoin are active in this test and are clinically effective in man.

By virtue of the antiarrhythmic activity, the compounds of Formula I and II are useful in treating arrhythmias in mammals. A physician or veterinarian of ordinary skill could readily determine a subject who exhibits arrhythmias.

Regardless of the route of administration selected, the compounds of the present invention are formulated into pharmaceutically acceptable dosage forms by conventional methods known to the pharmaceutical art.

The compounds can be administered in such oral unit dosage forms as tablets, capsules, pills, powders, or granules. They also may be administered intraperitoneally, subcutaneously, or intramuscularly, using forms known to the pharmaceutical art. In general, the preferred form of administration is oral.

An effective but non-toxic quantity of the compound is employed in treatment. The dosage regimen for preventing or treating arrhythmia by the compounds of this invention is selected in accordance with a variety of factors including the type, age, weight, sex, and medical condition of the patient, the severity of the arrhythmia, the route of administration and the particular compound employed. An ordinarily skilled physician or veterinarian will readily determine and prescribe the effective amount of the antiarrhythmic agent to prevent or arrest the progress of the condition. In so proceeding, the physician or veterinarian could employ relatively low dosages at first, subsequently increasing the dose until a maximum response is obtained.

Initial dosages of the compounds of the invention are ordinarily in the area of 3 to 5 mg/kg up to about 50 mg/kg orally.

The compounds of this invention can also be administered as pharmacologically acceptable acid addition salts such as the hydrochloride, hydrobromide, hydroiodide, sulfate, phosphate, acetate, propionate, lactate, maleate, malate, succinate, tartrate and the like. Additionally, the compounds of this invention may be administered in a suitable hydrated form.

The compounds of this invention are prepared from 10-hydroxymethyl steroids (i.e., 19-hydroxysteroids), compounds of Formula XI, which have been suitably protected at other functionalities for ensuing reactions. During the course of these procedures these protecting groups and functional groups can be altered by appropriate means known in the art as required for the desired reactions. The 10-hydroxymethyl steroids, XI, are oxidized by methods known to those skilled in the art to the corresponding 10-aldehydes, Formula XII, using strongly oxidizing inorganic compounds. A preferred oxidizing agent is chromium trioxide in an organic medium such as pyridine or acetone. The 10-aldehydes thus formed can be converted to the aminoalkyl compounds of this invention, Formula I, by several methods, such as those illustrated in Charts A and B. Chart A: Reaction of the aldehydes, XII, with tosylmethyl isocyanide, followed by reduction of the intermediate nitriles, XIII, affords 2-aminoethyl compounds, Formula XIV, in which the carbon chain at the 10-position of the steroid has been extended by one carbon. The nitriles, XIII, can be reduced with active metal hydrides, such as lithium aluminum hydride and sodium borohydride, or by catalytic hydrogenation over transition-metal catalysts, such as palladium and rhodium. A preferred reducing agent is lithium aluminum hydride. Chart B: Reaction of the aldehydes, XII, with acetonitrile in the presence of strong base, such as butyl lithium, affords the nitrile intermediates, XXI. Reduction of these nitriles, as described above for Chart A, affords 1-hydroxy-3-aminopropyl compounds of Formula XXII.

The 10-aldehydes, XII, can also be homologized to extend the carbon chain, for example by the method of Chart C: The aldehyde group of compounds of Formula XII is converted by a Wittig reaction, using, for example, triphenylmethylphosphonium bromide, to the corresponding ethylene group. Intermediate alkenes, XXXI, thus formed are in turn converted by a hydroboration procedure to 2-hydroxyethyl compounds of Formula XXXII. For example, an alkene of Formula XXXI can react with diborane to form a normally unisolated intermediate which is oxidized with hydrogen peroxide in basic medium to the desired alcohol. Hydroxyalkyl steroids formed in this way can subsequently be oxidized as described above to the corresponding aldehydes, Formula XXIV. These aldehydes can then be converted to aminoalkyl steroids by the methods of Charts A or B, or by other methods, such as that illustrated in Chart D. Chart D: Aldehydes of Formula XLI are converted by reaction with hydroxylamine to corresponding oximes, XLII. Such oximes are subsequently converted to amines of Formula XLIII by reaction with active hydride reducing agents, such as lithium aluminum hydride.

The various 10-aminoalkyl steroids described above can be further modified by acylation to corresponding amides, LI, as illustrated in Chart E. Appropriate acylating agents include acyl halides, such as acetyl chloride and benzoyl chloride, or acid anhydrides, such as acetic anhydride and benzoic anhydride; appropriate solvent systems for the acylations include pyridine and mixtures of tertiary amines, such as triethylamine and N-methylmorpholine, in an unreactive organic solvent such as dichloromethane. These amides, Formula LI, can in turn be reduced to corresponding alkylamines of Formula LIII using active hydride compounds, such as lithium aluminum hydride. Repetition of the acylation and reduction procedures can afford various new compounds, such as those of Formulas LIV and LV, illustrated by Chart E. Alkylation of the tertiary amines of Formula LV affords quaternary ammonium compounds of Formula LVI. Examples of alkylating agents include alkyl halides, such as methyl bromide and ethyl chloride, and alkyl sulfates, such as dimethyl sulfate.

Cyclic compounds of Formula II are derived from compounds of Formula I having a carbon-carbon double bond centered at the 5-position, such as compounds of Formula LXI shown in Chart F. For example, compounds of Formula LXI can be converted in acidic media, such as concentrated aqueous hydrochloric acid, to cyclic derivatives, LXII. These cyclic compounds can in turn be derivatized by methods known to those skilled in the art. For example, the amides of Formula LXII ($R_{14}$=acyl) can be reduced by methods described in the above paragraphs to corresponding N-alkyl substituted compounds, Formula LXIII.

10-(Aminoalkenylene) steroids, of Formula LXXIII, in which the side chains are unsaturated, can be prepared from hydroxyalkyl steroids, as illustrated in Chart G. For example 2-cyano-1-hydroxyethyl steroids, Formula XXI, are converted by acetylation to the corresponding 2-acetoxy compounds, Formula LXXI. Appropriate acetylating reagents include acetic anhydride or acetyl chloride; appropriate solvent systems include pyridine and mixtures of tertiary amines, such as triethylamine and N-methylmorpholine, in an unreactive organic solvent such as dichloromethane. A preferred set of reagents is acetic anhydride in pyridine. Acetoxy compounds, LXXI, are heated in the presence of a base, such as a carbonate salt of an alkali or alkaline earth metal, in a moderately high-boiling inert organic solvent, such as a substituted aromatic hydrocarbon or an alkyl polyether, to form alkenylene nitriles, Formula LXXII. Preferred conditions include sodium carbonate in hot t-butylbenzene. The nitriles, LXXII, can be reduced to corresponding 3-amino-1-propenyl steroids, Formula LXXIII, using a selective reducing agent such as lithium aluminum hydride, as described above. The nitriles, LXXII, can also be reduced to corresponding 3-aminopropyl steroids, Formula LXXIV, by catalytic hydrogenation, as described above. Exhaustive conditions, such as hydrogenation over palladium at elevated temperatures for an extended time, will reduce the carbon-carbon double bond of the steroid ring system; less exhaustive conditions known in the art permit isolation of 3-aminopropyl steroids retaining the ring double bond.

The following examples further illustrate details for the preparation of the compound of the invention. The invention, which is fully set forth in the foregoing disclosure is not to be construed as being limited either in spirit or scope by these examples. Those skilled in the art will readily understand that known variations of the conditions and processes of the following preparative procedures can also be used to prepare the compounds of the invention. All temperatures are in degrees celsius unless otherwise noted.

EXAMPLE 1

19-Acetoxyandrost-4-ene-3,17-dione

19-Hydroxyandrost-4-ene-3,17-dione (50 g) dissolved in 100 ml of pyridine and 250 ml of acetic anhydride was swirled while being warmed on a steam bath. When solution was complete, the reaction was allowed to stand at room temperature. After two hours ice and water were added and the resultant oil was extracted into ethyl acetate. The organic phase was washed with water, dried over sodium sulfate, filtered, and concentrated in vacuo to give 58 g of the title compound as an amorphous solid. The product, homogeneous by thin-layer chromatography using 1:1 ethyl acetate/Skellysolve B on silica gel, was employed for subsequent reactions without further purification.

EXAMPLE 2

19-Hydroxyandrost-5-ene-3,17-dione, cyclic bis(1,2-ethanediyl acetal)

The acetate ester of Example 1, 500 ml of ethylene glycol, and 500 mg of p-toluenesulfonic acid were combined under nitrogen and stirred rapidly. The mixture was heated slowly as the pressure was reduced to 2 mm Hg until ethylene glycol began to distill slowly. Temperature and pressure were maintained for 6 hours as 350 ml of distillate collected. The mixture was cooled to about 50° and then treated with 20 g of sodium hydroxide in 300 ml of methonol. The mixture was maintained at 50° under reduced pressure as 150 ml of methanol distilled. After standing overnight the mixture was treated, with stirring, with 50 ml of water and the resultant solid collected by filtration. The solid was washed with 10% aqueous methanol and dried overnight under high vacuum at 50° to give 44.2 g of the title compound. The product, homogeneous by thin-layer chromatography (see Example 1), was used for subsequent reactions without further purification.

EXAMPLE 3

19-Hydroxyandrost-5-ene-3,17-dione, cyclic bis(1,3-propanediyl acetal)

The acetate ester of Example 1 (50 g) and 500 m ml of 1,3-propanediol in 500 ml of toluene were dried by evaporation of part of the solvent. Oxalic acid (1.2 g) was added and the solution heated for about three days. Upon cooling residual propanediol separated and was discarded. The toluene layer was diluted with benzene, washed with cold dilute aqueous potassium carbonate and two portions of brine, dried over magnesium sulfate, filtered, and concentrated in vacuo. The crude product was further purified by column chromatography on silica gel, giving 30 g of the acetal acetate ester. A portion of the acetate ester was dissolved in methanol and heated at reflux for two hours with aqueous sodium hydroxide. After standing at room temperature overnight, the reaction mixture afforded crystalline material which was collected, washed, and recrystallized from acetone, giving the title compound. Structure assignment was supported by ultraviolet and infrared spectra and by elemental analysis.

EXAMPLE 4

19-Oxoandrost-5-ene-3,17-dione, cyclic bis(1,2-ethanediyl acetal)

To 440 ml of pyridine kept under a nitrogen atmosphere at −10° was added, with stirring over a 15 min period, chromium trioxide (44 g). The 19-hydroxy steroid of Example 2 (44 g) was added with rapid stirring, and the mixture stirred at −5° for two hours and then for 2.5 hours at room temperature. The mixture was maintained at 25° to 30° in an acetone-ice bath while 400 ml of a 45% sodium bisulfite solution was added. After the mixture stood overnight, a white solid was collected by filtration and dried under high vacuum, giving 31 g of the title compound, homogeneous by thin-layer chromatography (see Example 1). Structure assignment was supported by infrared and nmr spectra.

EXAMPLE 5

19-Oxoandrost-5-ene-3,17-dione, cyclic bis(1,3-propanediyl acetal)

The title compound was prepared by the method of Example 4 using 6 g of the 19-hydroxy steroid of Example 3. Recrystallization from benzene afforded 1.8 g of the crystalline product. Structure assignment was supported by the infrared spectrum and by elemental analysis.

EXAMPLE 6

19-Cyanoandrost-5-ene-3,17-dione, cyclic bis(1,2-ethanediyl acetal)

To a stirred solution of 15 g of tosylmethylisocyanide in a 125 ml of dimethoxyethane at −15° was added rapidly 25 g of potassium t-butoxide. After a few minutes 2 ml of methanol and, batchwise, 16 g of the product aldehyde of Example 4 were added. The reaction was stirred for 30 min at −15° and then allowed to warm to room temperature and to stand overnight. The reaction mixture was poured over ice and vigorously stirred. The precipitate was collected, washed with water, and dried to give 15.1 g of the title compound. Structure assignment was confirmed by nmr, ultraviolet, and infrared spectra.

EXAMPLE 7

19-Cyanoandrost-5-ene-3,17-dione, cyclic bis(1,3-propanediyl acetal)

The title compound was prepared by the method of Example 6 using 3.1 g of the product aldehyde of Example 5. Recrystallization from isopropyl alcohol afforded 2.3 g of the crystalline product. Structure assignment was supported by the infrared spectrum and by elemental analysis.

EXAMPLE 8

19-Cyanoandrost-4-ene-3,17-dione

To a solution of 1.2 g of the nitrile of Example 6 in 25 ml of acetone was added a mixture of 2 ml of perchloric acid, 3 ml of water, and 5 ml of acetone. The mixture was stirred until solution was complete and then allowed to stand overnight. The solution was clarified by filtration, diluted to about 100 ml, and allowed to stand until crystals had formed. The crystalline solid was collected and dried under vacuum to give 0.8 g of the title compound, homogeneous by thin-layer chromatography (ethyl acetate on silica gel). Structure assignment was confirmed by nmr and ultraviolet spectra.

EXAMPLE 9

10-(2-Aminoethyl)estr-5-ene-3,17-dione, cyclic bis(1,2-ethanediyl acetal), hydrochloride monohydrate To a stirred mixture of 1 g of lithium aluminum hydride in 100 ml of refluxing diethyl ether was added dropwise a solution of 1 g of the nitrile of Example 6 in 10 ml each of diethyl ether and dioxane. After two hours 1 ml of water in 5 ml of dioxane was added dropwise, followed by 1.8 ml of 20% aqueous sodium hydroxide and 3 ml of water. After stirring overnight, the solution was filtered through a filtering aid and the filtrate concentrated in vacuo to an oil. The oil was dissolved in diethyl ether and carefully acidified with HCl in dioxane. The gelatinous solid was collected, washed with diethyl ether, and dried under vacuum, giving 0.7 g of the title compound. Structure assignment was confirmed by nmr and infrared spectra and by elemental analysis.

EXAMPLE 10

10-(2-Aminoethyl)estr-5-ene-3,17-dione, cyclic bis(1,2-ethanediyl acetal), acetate (salt)

The title compound was prepared according to the method of Example 9, except that acetic acid was used in place of HCl. Structure assignment of the acetate salt was confirmed by the nmr spectrum and by elemental analysis.

EXAMPLE 11

10-(2-Aminoethyl)estr-5-ene-3,17-dione, cyclic bis(1,3-propanediyl acetal), acetate (salt)

The title compound was prepared by the method of Example 10 using the nitrile product of Example 7. The acetate salt precipitated instantly upon addition of the acetic acid, giving 0.4 g of the crystalline solid. Structure assignment was supported by the infrared spectrum and by elemental analysis.

EXAMPLE 12

10-(2-Aminoethyl)estrane-3,17-dione, cyclic bis(1,2-ethanediyl acetal), acetate (salt)

A solution of 5 g of the compound of Example 10 in isopropyl alcohol containing a few drops of triethylamine was hydrogenated over platinum oxide at 60 psi and 60° until hydrogen uptake was complete. Insolubles were removed by filtration and the solution concentrated in vacuo to an oil, which was redissolved in diethyl ether and acidified with acetic acid. The solid was collected and dried, giving 3.5 g of the title compound. Structure assignment was supported by nmr and ultraviolet spectra and by elemental analysis.

EXAMPLE 13

10-(2-Aminoethyl)estrane-3,17-dione, hydrochloride

To a stirred solution of the compound of Example 12 (2.0 g) in 50 ml of acetone was added 1 ml of 5N HCl in dioxane and 1 ml of water. After standing for 24 hours the solution was concentrated in vacuo to an amorphous solid, which was triturated with diethyl ether, filtered, and dried. Repeated triturations with diethyl ether afforded 1.7 g of the title compound. Structure assignment was confirmed by nmr and infrared spectra and by elemental analysis.

EXAMPLE 14

10-(2-Acetamidoethyl)estr-5-ene-3,17-dione, cyclic bis(1,2-ethanediyl acetal), Method A A solution of 2 g of the product amine of Example 9 in 25 ml of triethylamine and 10 ml of acetic anhydride was allowed to stand overnight. Water was added and the resultant solid collected, washed with water, and dried in a vacuum to give 2 g of the title compound. Structure assignment was confirmed by nmr and infrared spectra and by elemental analysis.

EXAMPLE 15

10-(2-Acetamidoethyl)estr-5-ene-3,17-dione, cyclic bis(1,2-ethanediyl acetal), Method B A solution of 10 g of the product amine of Example 10 and 20 ml of acetic anhydride in 100 ml of pyridine were swirled until solution was complete. After 30 min water was added while swirling the solution in a cooling bath until the point of crystallization. Crystals were collected, washed with water, and dried under vacuum at 50°, giving 8 g of the title compound, homogeneous by thin-layer chromatography. The compound prepared by this method is identical with that prepared by Example 14.

EXAMPLE 16

10-[2-(Ethylamino)ethyl]estr-5-ene-3,17-dione, cyclic bis(1,2-ethanediyl acetal)

To a mixture of 8 g of lithium aluminum hydride in 50 ml of dioxane was added, with stirring, 8 g of the amide of Example 15. After the initial vigorous reaction had settled down, the mixture was heated at reflux for three hours. Water (8 ml) diluted in 25 ml of dioxane was added dropwise, followed by 7 ml of 20% aqueous sodium hydroxide and 25 ml of water. The resultant mixture was diluted with two volumes of diethyl ether, filtered to remove insoluble material, and concentrated in vacuo to a colorless oil. The oil was crystallized from diethyl ether acidified with an equivalent amount of acetic acid, giving 7.7 g of the title compound as a solid. Structure assignment was confirmed by nmr and infrared spectra and by elemental analysis.

EXAMPLE 17

10-[2-(N-Ethylacetamido)ethyl]estr-5-ene-3,17-dione, cyclic bis(1,2-ethanediyl acetal)

The title compound was prepared by the method of Example 15 using the product compound of Example 16. The initially isolated oil solidified, giving 6.1 g of a crystalline solid. Structure assignment was supported by the nmr spectrum and by elemental analysis.

EXAMPLE 18

10-[2-(N,N-Diethylamino)ethyl]estr-5-ene-3,17-dione, cyclic bis(1,2-ethanediyl acetal)

The title compound was prepared by the method of Example 16 using the product amide of Example 17. Structure assignment was confirmed by the nmr spectrum and by elemental analysis.

EXAMPLE 19

N,N-Diethyl-N-methyl-[3,3:17,17-bis(1,2-ethanediylbis-(oxy))estran-10-yl]ethanaminium bromide To a solution of the amine of Example 18 (1.5 g) in 20 ml of acetone was bubbled methyl bromide. The solid which formed was collected, washed with diethyl ether, and dried, giving the title compound. Structure assignment was confirmed by the nmr spectrum and by elemental analysis.

EXAMPLE 20

19-Hydroxyiminoandrost-5-ene-3,17-dione, cyclic bis(1,2-ethanediyl acetal)

A mixture of 10 g of the aldehyde product from Example 4 and 10 g of hydroxylamine hydrochloride in 50 ml of pyridine was heated on a steam bath until solids were dissolved. The resultant two-phase system was stirred with heating until reaction was complete, about 90 min. Upon addition of water a solid separated which was collected, washed with water, and dried in vacuo at 50°. The title compound (10 g) was used for the next reaction without further purification.

EXAMPLE 21

19-Aminoandrost-5-ene-3,17-dione, cyclic bis(1,2-ethanediyl acetal), hydrochloride A solution of 10 g of the oxime from Example 20 in 100 ml of dioxane was added to a suspension of 10 g of lithium aluminum hydride in 200 ml of 1:1 diethyl ether/dioxane. After addition of the hydride, diethyl ether was slowly distilled away and the remaining mixture was heated at reflux for a day. To the reaction mixture were added dropwise 10 ml of water in 20 ml of dioxane, 8 ml of 20% aqueous sodium hydroxide, and 30 ml of water. Insolubles were removed by filtration and the filtrate reduced to an oil in vacuo. The oil was dissolved in diethyl ether and acidified with a few drops of 5N HCl in dioxane. The solid which formed was collected, washed, and dried to give the title compound. Structure assignment was supported by the nmr spectrum and by elemental analysis.

EXAMPLE 22

10-(2-Cyano-1-hydroxyethyl)estr-5-ene-3,17-dione, cyclic bis(1,2-ethanediyl acetal)

To a solution of 5 g of diisopropylamine in 25 ml of tetrahydrofuran was added dropwise under nitrogen 25 ml of 2M butyllithium in hexane. The freshly prepared lithium diisopropylamide was added dropwise with rapid stirring to 4 g of acetonitrile in 30 ml of tetrahydrofuran cooled to −60°. After the resultant solution was stirred for one hour, 7.1 g of the aldehyde product from Example 4 in 20 ml of tetrahydrofuran was added dropwise with rapid stirring. The reaction mixture was poured into ice with stirring. Volatiles were removed in vacuo, leaving a suspension of a solid in aqueous medium. The solid was collected, washed with water, and dried in a vacuum at 50° to give 6 g of the title compound. Structure assignment was confirmed by the nmr spectrum and by elemental analysis.

EXAMPLE 23

10-(3-Amino-1-hydroxypropyl)estr-5-ene-3,17-dione, cyclic bis(1,2-ethanediyl acetal), hydrochloride hemihydrate The title compound was prepared according to the method of Example 9 using 6 g of lithium aluminum hydride in 250 ml of diethyl ether and 5.5 g of the nitrile from Example 22 in 20 ml of dioxane. The resultant oil in diethyl ether was acidified with 3 ml of 5N HCl in dioxane, and the solid which formed was collected, washed, and dried, giving 5.1 g of the title compound. Structure assignment was supported by the nmr spectrum and by elemental analysis.

EXAMPLE 24

10-(3-Amino-1-hydroxypropyl)estr-5-ene-3,17-dione, cyclic bis(1,2-ethanediyl acetal), acetate (salt)

The title compound was prepared according the method of Example 23, except that acetic acid was used in place of HCl. Structure assignment was supported by the nmr spectrum and by elemental analysis.

EXAMPLE 25

19-Cyanocholest-5-en-3β-ol

The title compound was prepared by the method of Example 6 from 3β-acetoxy-19-oxacholest-5-ene, which was derived by acetylation of the corresponding 3-hydroxysteroid. Structure assignment was supported by the nmr spectrum and by elemental analysis.

EXAMPLE 26

10-(2-Aminoethyl)-19-norcholest-5-en-3β-ol, hydrochloride

The title compound was prepared by the method of Example 9 from 5 g of the nitrile of Example 25. An initially isolated white solid was taken up in hot methanol, filtered, and acidified with HCl in dioxane, and induced to recrystallize by the addition of ethyl acetate. The solid was collected and dried to give 4.1 g of the title compound. Structure assignment was supported by the nmr spectrum and by elemental analysis.

EXAMPLE 27

10-(2-Cyano-1-hydroxyethyl)-19-norcholest-5-en-3β-ol

The title compound was prepared by the method of Example 22 using 9 g of 3β-acetoxy-19-oxacholest-5-ene. The final addition of water (200 ml) afforded a solid which was filtered, washed with water, and dried to give 9 g of the title compound. The nitrile was used without further purification.

EXAMPLE 28

10-(3-Amino-1-hydroxypropyl)-19-norcholest-5-en-3β-ol, hydrochloride

The title compound was prepared by the method of Example 23 (and Example 9) using the nitrile of Example 27. Structure assignment of the isolated product was confirmed by the nmr spectrum and by elemental analysis.

EXAMPLE 29

10-(4-Amino-1-hydroxy-2-butynyl)-19-norcholest-5-en-3β-ol

To 80 ml of 2M butyllithium (in hexane) in 150 ml of tetrahydrofuran at −5° was added dropwise 7.5 ml of propargylamine. The mixture was allowed to warm to room temperature and then was recooled for the addition of 17.5 g of 3β-acetoxy-19-oxacholest-5-ene. The reaction mixture was allowed to warm to room temperature and to stand overnight. After the reaction was quenched with 100 ml of cold water, the reaction was extracted with diethyl ether. The ether layer was separated and washed with 3% aqueous hydrochloric acid, giving a separation into aqueous and ether layers separated by an oily interphase. The oily interphase solidified under fresh diethyl ether, and the ether layer produced a solid upon acidification with HCl in dioxane, each solid being the hydrochloride salt; and the aqueous layer produced a precipitate upon standing, the free base. The separate components, as the salt or free base, were purifiable by column chromatography using methanol/dichloromethane on silica gel. The title compound was isolated as the free base by concentrating the appropriate eluate fractions to give a solid product. Structure assignment was supported by the nmr spectrum and by elemental analysis.

EXAMPLE 20

(3aS, 3bS, 5aS, 8aS, 8bR, 10aS)-Dodecahydro-5a-methyl-1H,6H-3a,10a-butanoindeno[5,4-e]indole-6,12-dione A mixture of 1 g of the compound of Example 9 or 10 in 3 ml of concentrated aqueous hydrochloric acid was allowed to stand until solution was complete. The solution was concentrated in vacuo to an oily residue which was dissolved in acetone and precipitated with diethyl ether. The sticky solid was isolated by decanting, redissolved in methanol/dichloromethane, and diluted with ethyl acetate until turbid. The crystalline solid obtained was recrystallized from dichloromethane/ethyl acetate to give the title compound. Structure assignment was supported by nmr and mass spectra and by elemental analysis.

EXAMPLE 31

(3aS, 3bS, 5aS, 8aS, 8bR, 10aS)-1-Acetyldodecahydro-5a-methyl-1H,6H-3a,10a-butanoindeno[5,4-e]indole-6,12-dione The amide product prepared by the method of Example 14 or 15 was dissolved in 110 ml of acetone to which was added 2 ml of concentrated aqueous hydrochloric acid and 20 ml of water, and the mixture stirred until dissolved. After standing overnight the solution was concentrated in vacuo to remove acetone and then allowed to stand until crystals formed. The solid was collected, washed with water, and dried under vacuum at 40°, giving 8 g of the title compound, homogeneous by thin-layer chromatography using ethyl acetate on silica gel. Structure assignment was confirmed by the nmr spectrum and by elemental analysis.

EXAMPLE 32

(3aS, 3bS, 5aS, 8aS, 8bR, 10aS)-1-Acetyldodecahydro-5-a-methyl-1H,6H-3a,10a-butanoindeno[5,4-e]indole-6,12-diol, hemihydrate A solution of 2 g of the cyclized amide dione of Example 31 and 2 g of sodium borohydride in 50 ml of methanol and 5 ml of water was stirred for 15 min, and the volatiles removed in vacuo. The residual solid was triturated with water, filtered, and dried, giving 1.2 g of the title compound. Structure assignment was supported by nmr and infrared spectra and by elemental analysis.

EXAMPLE 33

(3aS, 3bS, 5aS, 8aS, 8bR, 10aS)-1-Ethyldodecahydro-5a-methyl-1H,6H-3a,10a-butanoindeno[5,4-e]indole-6,12-diol, hydrochloride hemihydrate The title compound was prepared according to the method of Example 16 using 5 g of the cyclized amide dione of Example 31. The initially isolated amorphous solid was dissolved in ethyl acetate and concentrated in vacuo to an oil which was acidified with HCl in dioxane, recrystallized from isopropyl alcohol/ethyl acetate, and dried at 100°. Structure assignment was confirmed by the infrared spectrum and by elemental analysis.

EXAMPLE 34

(3aS, 3bS, 5aS, 8aS, 8bR, 10aS)-6,12-Diacetoxy-1-ethyldodecahydro-5a-methyl-1H,6H-3a,10a-butanoindeno[5,4-e]indole, hydrochloride A solution of 1.1 g of the product diol of Example 33 in 1 ml of pyridine and 3 ml of acetic anhydride was allowed to stand for two hours. Water was added and the oil which separated was extracted with diethyl ether. The ether extract was washed with water, dried over sodium sulfate, filtered, and concentrated in vacuo to an oil. The oil was dissolved in diethyl ether and acidified with HCl in dioxane, giving a solid which was collected and dried under vacuum at 40°. Structure assignment of the title compound (0.75 g) was supported by the nmr spectrum and by elemental analysis.

EXAMPLE 35

19-Hydroxyandrostane-3,17-dione, cyclic bis(1,2-ethanediyl mercaptole)

A solution of 24.6 g of 19-acetoxyandrostane-3,17-dione, 100 g of ethanediol, 28 ml of ethyl orthoformate, and 1.5 g of p-toluenesulfonic acid in 280 ml of methanol was stirred at room temperature for three days. Aqueous potassium hydroxide was added dropwise to the rapidly stirred reaction mixture, which was maintained at 40°. After four hours the reaction was diluted with water and extracted with 1:1 diethyl ether/ethyl acetate. The organic phase was washed with 10% aqueous sodium carbonate, dried over sodium sulfate, and concentrated to an oil in vacuo. The residue was suspended in methanol and treated with 10 g of potassium hydroxide in 25 ml of water. After two hours water was added slowly, and the solid which separated was collected, washed with water, and dried, giving 30.1 g of the title compound.

EXAMPLE 36

19-Oxoandrostane-3,17-dione, cyclic bis(1,2-ethandiyl mercaptole)

A solution of 11.7 g of the thioacetal product of Example 35 in 300 ml of acetone was treated with 7 ml of chromium trioxide/sulfuric acid solution (4 mmolar) added dropwise at −20°. Acetone was removed and water was added. The mixture was extracted with diethyl ether and the organic layer washed with dilute aqueous potassium bicarbonate. The ether layer was dried over sodium sulfate, filtered, and concentrated to an oil, which was purified by high performance column chromatography on silica gel. The aldehyde was used without further purification in subsequent reactions.

EXAMPLE 37

10-(2-Aminoethyl)estrane-3,17-dione, cyclic bis(1,2-ethanediyl mercaptole)

The title compound is prepared by the methods of Example 6 and 9 using the aldehyde product of Example 36.

EXAMPLE 38

19-Hydroxyestrane

A mixture of 10 g of the thioacetal product of Example 35 and 60 g of W-2 Raney nickel in 500 ml of ethanol was heated at reflux under nitrogen for 24 hours. The catalyst was removed by filtration and the filtrate concentrated in vacuo to an oil. The oil was taken up in diethyl ether, filtered, and concentrated to give 6 g of the title compound as an oil.

EXAMPLE 39

19-Oxoestrane

The title compound (4.5 g) was prepared as an oil by the method of Example 36 using 6 g of the product compound of Example 38.

EXAMPLE 40

10-(2-Aminoethyl)estrane

The title compound is prepared by the methods of Examples 7 and 9 using the aldehyde product of Example 39.

EXAMPLE 41

10-(2-Aminoethyl)-3,3-(1,2-ethanediylbis(oxy))estr-5-ene-17-one

The product amine acetate of Example 10 (3 g) was heated at reflux in 100 ml of water for three hours. After cooling, the solution was filtered through a filtering aid and made basic with 20% aqueous sodium hydroxide. The oil which separated, upon standing, solidified to give 2.1 g of the title compound. Structure assignment was confirmed by infrared, ultraviolet, and nmr spectra. The compound was used for subsequent reactions without further purification.

EXAMPLE 42

10-(2-Acetamidoethyl)-3,3-(1,2-ethanediylbis(oxy))estr-5-ene-17-carboxaldehyde The amino group of the title compound of Example 41 was acetylated by the method of Example 15 for use without further purification in the subsequent reaction. Sodium hydride (1.2 g, 50% in oil dispersion) is washed with petroleum ether and dried under a stream of nitrogen. Trimethylsulfoxonium iodide (5 g) is mixed with the sodium hydride and cooled to −10°. Dimethylsulfoxide (40 ml) is added dropwise, and the mixture warmed and stirred at room temperature for 30 minutes. The mixture is cooled again to −10°, the steroid amide is added, and the reaction is allowed to proceed with stirring for about 40 hours. Water is added and the mixture extracted with diethyl ether. The ether layer is washed with water, dried over sodium sulfate, and concentrated to dryness. The intermediate epoxide thus formed is treated with borontrifluoride etherate in diethyl ether at 0°. The mixture is stirred at room temperature for about 15 minutes, diluted with ether, washed with 10% aqueous sodium bicarbonate, and concentrated to dryness. Purification of the resultant product by high performance liquid chromatography affords the title compound.

EXAMPLE 43

10-(2-Aminoethyl)-17-methoxycarbonyl-3,3-(1,2-ethanediylbis(oxy))estr-5-ene

The 17-carboxaldehyde of Example 42 is dissolved in acetone and cooled to −10°, then treated with 1.2 equivalents of standardized Jones reagent. The temperature is raised slowly to 10° and held for about one hour. The reaction is quenched with water, and the resultant crude product is taken up in chloroform, washed with water, dried over sodium sulfate, and concentrated to dryness in vacuo. The amide group of the intermediate product is removed by hydrolysis in 50 ml of refluxing 2N aqueous potassium hydroxide. After cooling, the solution is acidified with acetic acid. The resultant compound is collected and dried, then stirred in tetrahydrofuran to which is added diazomethane in ether. When solution is complete, the solvent is removed under vacuum, affording the title compound.

EXAMPLE 44

10-(2-Aminoethyl)-17α-(2-carboxyethyl)-3,3-(1,2-ethanediylbis(oxy))estr-5-ene-17-ol Potassium metal (18 g) is washed with toluene and t-amyl alcohol and then added to stirred refluxing t-amyl alcohol. When the potassium has completely dissolved and the solution cooled to 0°, acetylene is passed through the cold solution. The 17-ketone of Example 41, slurried in 150 ml of diethyl ether, is added rapidly and additional acetylene is passed through. After about 16 hours a solution of 50 g of ammonium chloride in 250 ml of water is added slowly, and the resultant mixture is extracted with 1:1 diethyl ether-ethyl acetate, washed with water, and concentrated in vacuo to give the 17-ethynyl intermediate. An exess of 3M methylmagnesium bromide in diethyl ether is added under a nitrogen atmosphere to about 350 ml of dry tetrahydrofuran, and the ethynyl compound, dissolved in 100 ml of tetrahydrofuran, is added with stirring. Stirring is continued overnight. A stream of carbon dioxide is then passed through the reaction mixture for about 20 hours, after which the reaction is quenched by pouring onto 1 liter of ice containing ammonium chloride. Organic volatiles are removed by evaporation in vacuo, and the resulting solid is collected by filtration and dried under vacuum. The residue is triturated with ammonium chloride, washed with water, collected, and dried to give the ethynyl carboxylic acid. The intermediate carboxylic acid is catalytically hydrogenated in ethanol using palladium on carbon as catalyst. After filtering and concentrating to dryness, the residue is dissolved in triethylamine, refiltered, and concentrated to dryness under high vacuum at 40°, giving the title compound.

EXAMPLE 45

3-[10-(2-Aminoethyl)-3,3-(1,2-ethanediylbis(oxy))estr-5-en-17α-yl]propanoic acid lactone The title compound is prepared from the 18 crown-6 ether complex of the product of Example 44 by reaction with acetic anhydride in dichloromethane containing triethylamine, using the basic method, for example, of *J. Chem. Soc., Chem. Commun.*, 471 (1978).

EXAMPLE 46

10-(2-Cyano-1-acetoxyethyl)estr-5-ene-3,17-dione, cyclic bis(1,2-ethanediyl acetal)

The title compound of Example 22 (10 g) in 50 ml of pyridine and 50 ml of acetic anhydride was heated on a steam bath for one hour and allowed to stand at room temperature overnight. The solution was poured with stirring over ice and the resultant oil was separated by decanting. The oil was induced to crystallize by resuspension in water, giving 10.2 g of the title compound. Structure assignment was supported by infrared and nmr spectra and by elemental analysis.

EXAMPLE 47

10-(2-Cyanoethenyl)estr-5-ene-3,17-dione, cyclic bis(1,2-ethanediyl acetal)

The acetylated compound of Example 46 (2.5 g) was dissolved in 25 ml of t-butylbenzene to which was added 2.5 g of anyhydrous sodium carbonate. After the mixture was stirred at reflux for ten hours, the solvent was removed and the residue was extracted into diethyl ether. The organic layer was washed with water, dried over sodium sulfate, and reduced to an oil under vacuum. Upon trituration with diethyl ether, the oil crystallized, giving 1.7 g of the title compound. Structure assignment was supported by the nmr spectrum and by elemental analysis.

EXAMPLE 48

10-(3-Amino-1-propenyl)estr-5-ene-3,17-dione, cyclic bis(1,2-ethanediyl acetal)

The title compound is prepared from the nitrile of Example 47 using the method of Example 9.

EXAMPLE 49

10-(2-Cyanoethyl)estr-5-ene-3,17-dione, cyclic bis(1,2-ethanediyl acetal)

The title compound of Example 47 is partially reduced by catalytic hydrogenation in ethanol using palladium on carbon as catalyst, giving the title compound.

EXAMPLE 50

10-(3-Aminopropyl)estr-5-ene-3,17-dione, cyclic bis(1,2-ethanediyl acetal), acetate (salt), Method A The title compound is prepared by the method of Example 9 using the nitrile product of Example 49.

EXAMPLE 51

10-Ethenylestr-5-ene-3,17-dione, cyclic bis(1,2-ethanediyl acetal)

The title compound is prepared from the aldehyde product of Example 4 by reaction with triphenylmethylphosphonium bromide in diethyl ether, using the method, for example, of *Organic Synthesis*, Vol. 40, p. 66 (1960).

EXAMPLE 52

10-(2-Hydroxyethyl)estr-5-ene-3,17-dione, cyclic bis(1,2-ethanediyl acetal)

The title compound is prepared from the product compound of Example 41 by rection with diborane, followed by reaction with hydrogen peroxide in aqueous base, using the method, for example, of *J. Org. Chem.*, 22, 1136 (1957).

EXAMPLE 53

10-(3-Aminopropyl)estr-5-ene-3,17-dione, cyclic bis(1,2-ethanediyl acetal), acetate (salt), Method B The title compound is prepared by the methods of Examples 2, 4, 6, and 9 from the product compound of Example 42.

EXAMPLE 54

10-(2-Aminoethyl)-5α-estrane-3,17-dione, hydrochloride

The title compound is prepared from 19-hydroxy-5α-androstane-3,17-dione using the methods of Examples 1, 2, 4, 6, 10, and 12.

EXAMPLE 55

10-(2-Aminoethyl)-5β-estrane-3,17-dione, hydrochloride

The title compound is prepared from 19-hydroxy-5β-androstane-3,17-dione using the methods of Examples 1, 2, 4, 6, 10, and 12.

EXAMPLE 56

10-[Cyano(trimethylsilyloxy)methyl]estr-5-ene-3,17-dione, cyclic bis(1,2-ethanediyl acetal)

The product of Example 4 (10 gms) was dissolved in 100 ml. of acetone cyanohydrin and warmed at 50° C.

for 3 hrs. The excess acetone cyanohydrin is removed under reduced pressure. Hexamethyldisilazane (50 ml.) was added and the resulting solution was heated for three hours on a steam bath while stirring. Vacuum distillation of the excess hexamethyldisilazane followed by crystallization of the residue from methanol afforded the title compound.

EXAMPLE 57

10-(2-Amino-1-hydroxyethyl)estr-5-ene-3,17-dione, cyclic bis(1,2-ethanediyl acetal), hydrochloride The title compound was prepared by the method of Example 9 using the nitrile product of Example 56. The material was purified by crystallization. The structure assignment was confirmed by the nmr spectrum and by elemental analysis.

EXAMPLE 58

10-[(2-Diethylamino)ethyl]estr-5-ene-3,17-dione, hydrochloride

The title compound was prepared by the method of Example 30 using the product of Example 18. Structure assignment was confirmed by the nmr spectrum and by elemental analysis.

CHART A

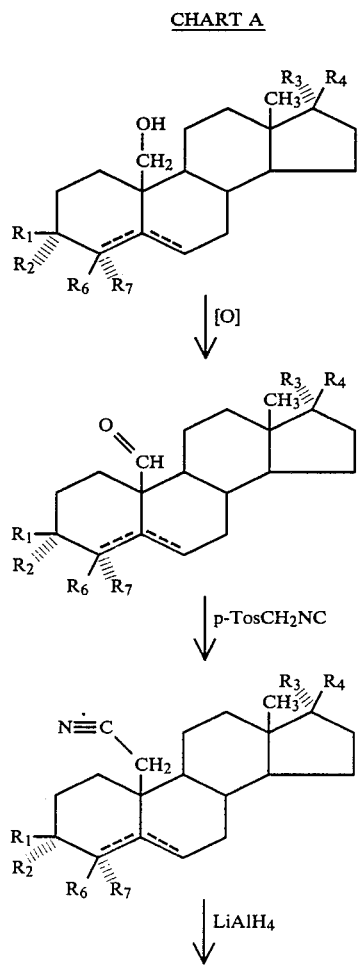

-continued
CHART A

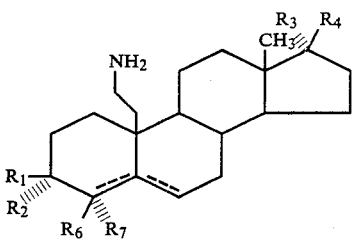

CHART B

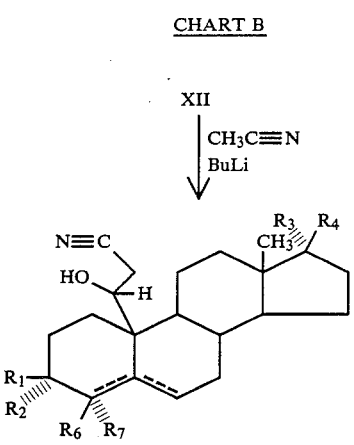

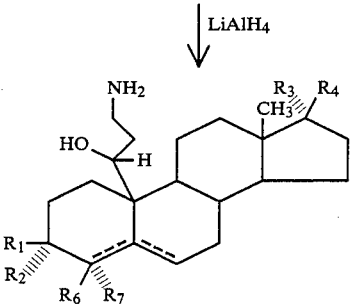

CHART C

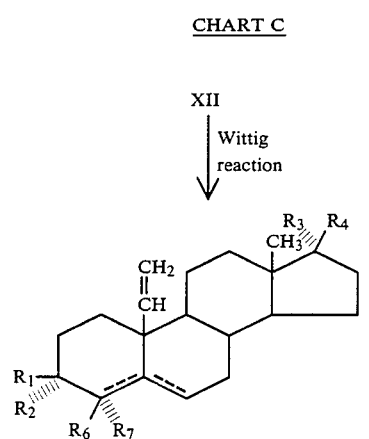

-continued
CHART C
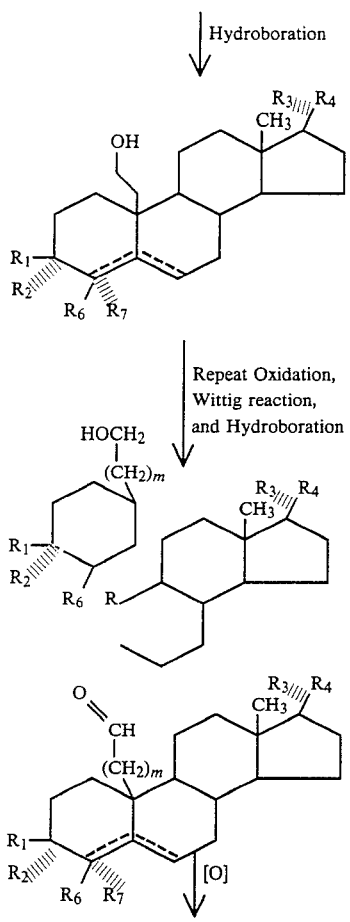
CHART D
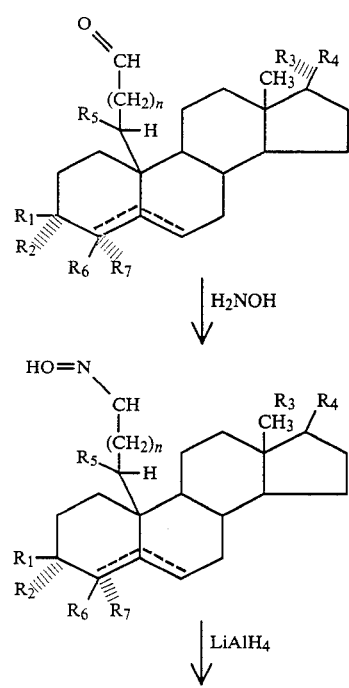
-continued
CHART D
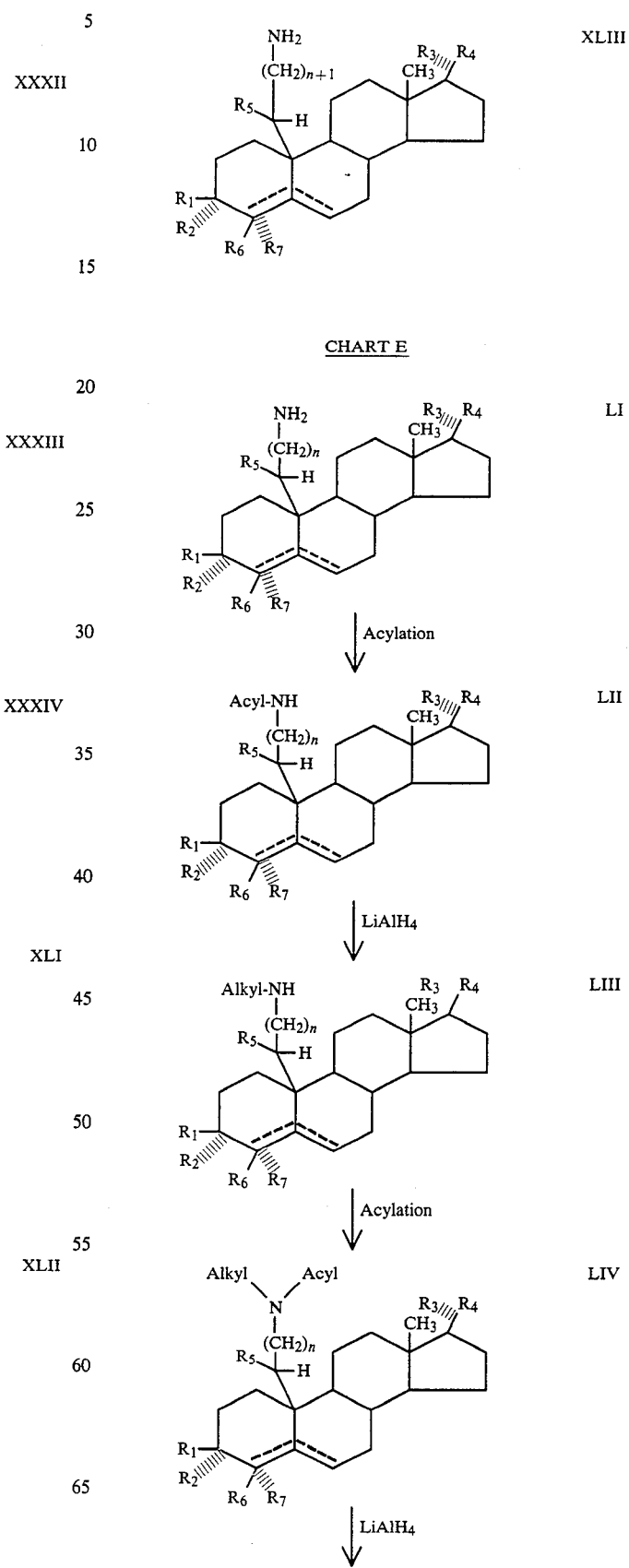

CHART E -continued
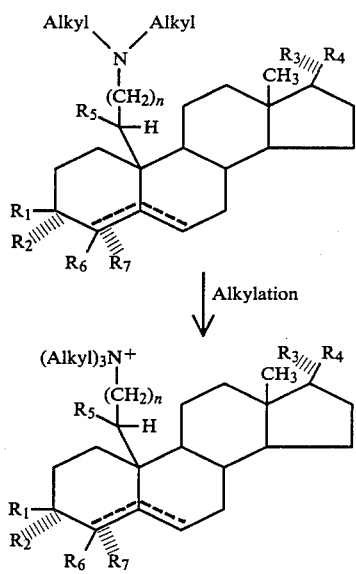
CHART F
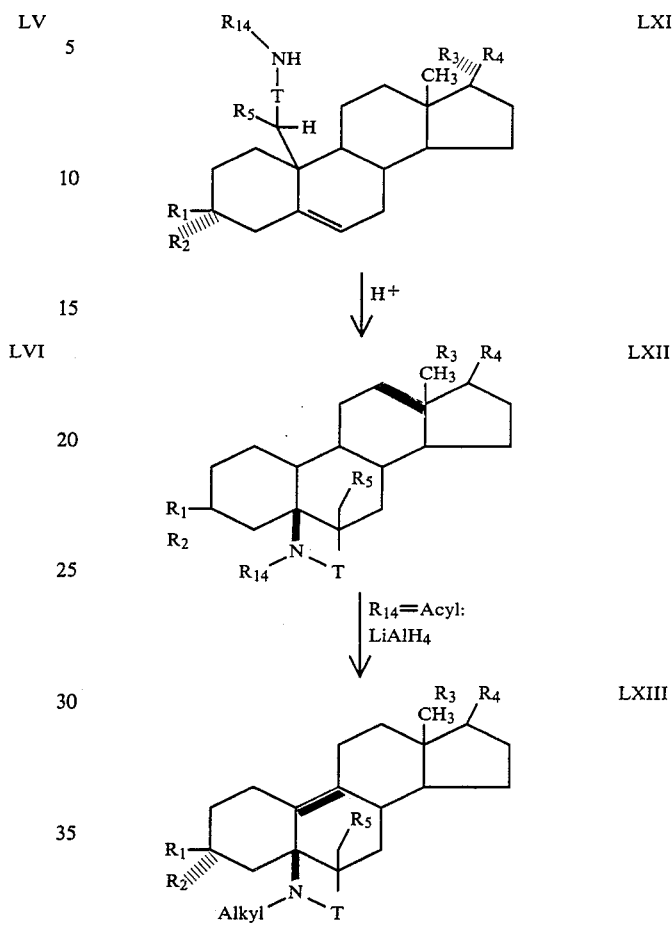
CHART G
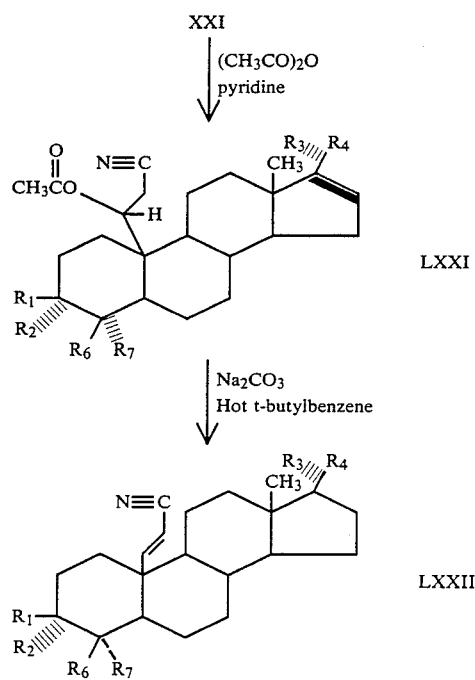

CHART G
-continued

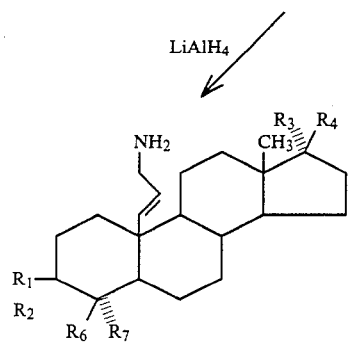

LXXIII

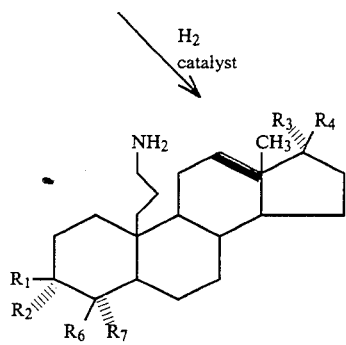

LXXIV

What I claim is:
1. A compound of the formula:

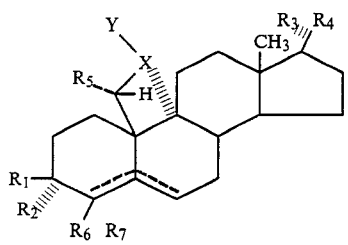

wherein $R_1$ and $R_2$, each being the same or different, are:
(a) hydrogen;
(b) benzyloxy;
(c) hydroxyl;
(d) alkanoyloxy as from one to six carbon atoms, inclusive;
(e) wherein $R_1$ and $R_2$ are taken together to form a keto group; or
(f) wherein $R_1$ and $R_2$ are taken together to form a heterocyclic ring of the formula:

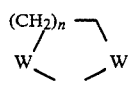

wherein W is oxygen or sulfur; wherein $n_1$ is 1 or 2.
wherein $R_3$ and $R_4$, each being the same or different are:
(a) hydrogen;
(b) alkyl from 1 to 10 carbon atoms, inclusive;
(c) alkanoyloxy of from 1 to 6 carbon atoms, inclusive;
(d) aralkoxy;
(e) hydroxy;
(f) wherein $R_3$ and $R_4$ are taken together to form:
(1) a keto group;

(2)

(g) wherein $R_3$ and $R_4$ are taken together to form a heterocyclic ring of the formula:

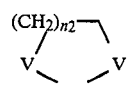

wherein V is oxygen or sulfur; wherein $n_2$ is 1 or 2;
(h) wherin one of $R_3$ or $R_4$ is of the formula:

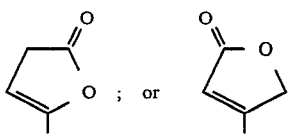

with the proviso that the remaining $R_3$ or $R_4$ is hydrogen;
(i) —COOR$_8$; or
(J) carboxyalkyl, of from 2 to 5 carbon atoms, inclusive;
wherein $R_8$ is:
(a) hydrogen; or
(b) alkyl of from 1 to 6 carbon atoms, inclusive;
wherein $R_5$ is:
(a) hydrogen;
(b) hydroxyl; or
(c) trialkylsilyloxy; with the proviso that $R_5$ is present only when the carbon to which it is attached is saturated;
wherein $R_6$ and $R_7$, each being the same or different, are:
(a) hydrogen; or
(b) alkyl of from 1 to 6 carbon atoms, inclusive, with the proviso that only one of $R_6$ or $R_7$ may be present when a 4,5 ring double bond exists;
wherein X is:
(a) alkyl of from 1 to 6 carbon atoms, inclusive;
(b) alkylidene of from 1 to 6 carbon atoms, inclusive, with the proviso that when X is alkylidene, $R_5$ is not present;
wherein Y is:
(a) —NR$_9$R$_{10}$; or
(b) —N$^{(+)}$R$_{11}$R$_{12}$R$_{13}$ Z$^{(-)}$;
wherein $R_9$ and $R_{10}$, each being the same or different, are:
(a) hydrogen;

(b) alkyl of from 1 to 6 carbon atoms, inclusive;
(c) alkanoyl of from 1 to 6 carbon atoms, inclusive;
(d) aryl; or
(e) aralkyl;

wherein $R_{11}$, $R_{12}$ and $R_{13}$, each being the same or different are:
(a) alkyl of from 1 to 6 carbon atoms, inclusive;
(b) aryl; or
(c) aralkyl;

wherein Z is a pharmacologically acceptable negative ion; or the pharmacologically acceptable salts; the compounds of the invention being either hydrated or unhydrated.

2. A compound according to claim 1 wherein $R_3$ and $R_4$, each being the same or different as:
(a) hydrogen; or
(b) alkyl of from 1 to 10 carbon atoms, inclusive.

3. 10-(2-Aminoethyl)estrane, a compound according to claim 2.

4. A compound according to claim 2 wherein one of $R_3$ and $R_4$ is hydrogen and the other of $R_3$ and $R_4$ is alkyl of from 1 to 10 carbon atoms, inclusive.

5. 10-(2-Aminoethyl)-19-norcholest-5-en-3β-ol, hydrochloride, a compound according to claim 3.

6. 10-(4-Amino-1-hydroxy-2-butyny)-19-norcholest-5-en-3β-ol, a compound according to claim 3.

7. 10-(3-Amino-1-hydroxypropyl)-19-norcholest-5-en-3β-ol, hydrochloride, a compound according to claim 3.

8. A compound according to claim 1 wherein $R_3$ and $R_4$ are taken together to form a heterocyclic ring of the formula:

$$\begin{array}{c}(CH_2)_n\\ / \quad \backslash \\ V \quad \quad V\end{array}$$

wherein V is oxygen or sulfur; wherein n is 1 or 2.

9. A compound according to claim 1 wherein $R_3$ and $R_4$ are taken together to form a heterocyclic ring of the formula:

$$\begin{array}{c}(CH_2)_n\\ / \quad \backslash \\ O \quad \quad O\end{array}$$

10. 10-(2-Amino-1-hydroxyethyl)estr-5-ene-3,17-dione, cyclic bis(1,2-ethanediyl acetal), hydrochloride, a compound according to claim 9.

11. 10-(2-Aminoethyl)estr-5-ene-3,17-dione, cyclic bis(1,2-ethanediyl acetal), hydrochloride, monohydrate, a compound according to claim 9.

12. 10-(2-Aminoethyl)estr-5-ene-3,17-dione, cyclic bis(1,2-ethanediyl acetal), acetate (salt), a compound according to claim 9.

13. 10-(3-Aminopropyl)estr-5-ene-3,17-dione, cyclic bis(1,2-ethanediyl acetal), acetate (salt), a compound according to claim 9.

14. 10-(2-Aminoethyl)-5α-estrane-3,17-dione, cyclic bis(1,2-ethanediyl acetal), acetate (salt), a compound according to claim 9.

15. 10-(2-Aminoethyl)-5β-estrane-3,17-dione, cyclic bis(1,2-ethanediyl acetal), acetate (salt), a compound according to claim 9.

16. 10-(2-Aminoethyl)estr-5-ene-3,17-dione, cyclic bis(1,3-propanediyl acetal), acetate (salt), a compound according to claim 9.

17. 10-[2-(Ethylamino)ethyl]estr-5-ene-3,17-dione, cyclic bis(1,2-ethanediyl acetal), a compound according to claim 9.

18. 10-(3-Amino-1-hydroxypropyl)estr-5-ene-3,17-dione, cyclic bis(1,2-ethanediyl acetal), hydrochloride hemihydrate, a compound according to claim 9.

19. 10-(3-Amino-1-hydroxypropyl)estr-5-ene-3,17-dione, cyclic bis(1,2-ethanediyl acetal), acetate (salt), a compound according to claim 9.

20. 19-Aminoandrost-5-ene-3,17-dione, cyclic bis(1,2-ethanediyl acetal), hydrochloride, a compound according to claim 9.

21. 10-[2-(N,N-Diethylamino)ethyl]estr-5-ene-3,17-dione, cyclic bis(1,2-ethanediyl acetal), a compound according to claim 9.

22. 10-(3-Amino-1-propenyl)estr-5-ene-3,17-dione, cyclic bis(1,2-ethanediyl acetal), a compound according to claim 9.

23. A compound according to claim 8 wherein $R_3$ and $R_4$ are taken together to form a heterocyclic ring of the formula:

$$\begin{array}{c}(CH_2)_n\\ / \quad \backslash \\ S \quad \quad S\end{array}$$

24. 10-(2-Aminoethyl)estrane-3,17-dione, cyclic bis(1,2-ethanediyl mercaptole) a compound according to claim 23.

25. A compound according to claim 9 wherein Y is $-N^{(+)}R_{11}R_{12}R_{13} Z^{(-)}$.

26. N,N-Diethyl-N-methyl-[3,3:17,17-bis(1,2-ethanediyl bis(oxy))estran-10-yl]ethanaminium bromide, a compound according to claim 25.

27. A compound according to claim 1 wherein $R_3$ and $R_4$ are taken together to form a keto group.

28. 10-(2-Aminoethyl)-5α-estrane-3,17-dione, hydrochloride, a compound according to claim 1.

29. 10-(-Aminoethyl)-5β-estrane-3,17-dione, hydrochloride, a compound according to claim 1.

30. 10-[(2-Diethylamino)ethyl]estr-5-ene-3,17-dione, hydrochloride, a compound according to claim 1.

31. 10-(2-Aminoethyl)-3,3-(1,2-ethanediylbis(oxy))-estr-5-ene-17-one, a compound according to claim 1.

32. A compound according to claim 1 wherein one of $R_3$ or $R_4$ is $-COOR_8$, the other being hydrogen.

33. 10-(2-Aminoethyl)-17-methoxycarbonyl-3,3-(1,2-ethanediyl-bis(oxy))estr-5-ene, a compound according to claim 32.

34. A compound according to claim 1 wherein one of $R_3$ or $R_4$ is carboxylalkyl of from 2 to 5 carbon atoms, inclusive.

35. 10-(2-Aminoethyl)-17α-(2-carboxyethyl)-3,3-(1,2-ethanediylbis(oxy))estr-5-ene-17-ol, a compound according to claim 34.

36. A compound according to claim 1 wherein $R_3$ and $R_4$ are taken together to form:

$$\begin{array}{c}\quad\quad O\\ \quad\quad \parallel \\ / \quad \backslash \\ \quad \quad O\end{array}$$

37. 3-[10-(2-Aminoethyl)-3,3-(1,2-ethanediylbis(oxy))-estr-5-en-17α-yl]propanoic acid lactone, a compound according to claim 36.

38. A compound of the formula:

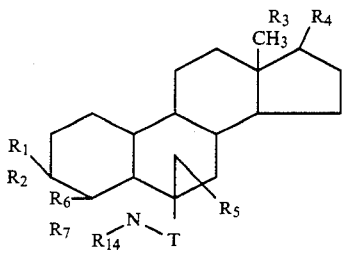

wherein $R_1$ and $R_2$, each being the same or different, are:
(a) hydrogen;
(b) benzyloxy;
(c) hydroxyl;
(d) alkanoyloxy of from one to six carbon atoms, inclusive;
(e) wherein $R_1$ and $R_2$ are taken together to form a keto group; or
(f) wherein $R_1$ and $R_2$ are taken together to form a heterocyclic ring of the formula:

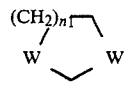

wherein W is oxygen or sulfur; wherein $n_2$ is 1 or 2;
wherein $R_3$ and $R_4$, each being the same or different are:
(a) hydrogen;
(b) alkyl of from 1 to 10 carbon atoms, inclusive;
(c) alkanoyloxy of from 1 to 6 carbon atoms, inclusive;
(d) aralkyl;
(e) hydroxy;
(f) wherein $R_3$ and $R_4$ are taken together to form:
(1) a keto group;

(2)
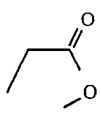

(g) wherein $R_3$ and $R_4$ are taken together to form a heterocyclic ring of the formula:

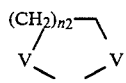

wherein V is oxygen or sulfur; wherein $n_2$ is 1 or 2;

(h) wherein one of $R_3$ or $R_4$ is of the formula:

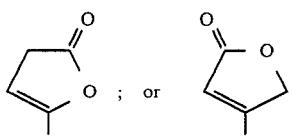

with the proviso that the remaining $R_3$ or $R_4$ is hydrogen;
(i) —COOR$_8$; or
(j) carboxyalkyl of from 2 to 5 carbon atoms, inclusive;
wherein $R_8$ is:
(a) hydrogen; or
(b) alkyl of from 1 to 6 carbon atoms, inclusive;
wherin $R_5$ is:
(a) hydrogen;
(b) hydroxyl; or
(c) trialkylsilyloxy;
wherein $R_6$ and $R_7$, each being the same or different, are:
(a) hydrogen; or
(b) alkyl of from 1 to 6 carbon atoms, inclusive with the proviso that only one of $R_6$ or $R_7$ may be present when a 4,5 ring double bond exists;
wherein T is —(CH$_2$)$_n$—; wherein n is an integer of from 1 to 2; wherin $R_{14}$ is:
(a) hydrogen;
(b) alkyl of from 1 to 6 carbon atoms; or
(c) alkanoyl of from 1 to 6 carbon atoms, inclusive.

39. A compound according to claim 38, wherein $R_3$ and $R_4$ are taken together to form a keto group.

40. A compound according to claim 39 wherein n is 1.

41. A compound according to claim 38, wherein said compound comprises 5,10-(iminoethano)estrane-3,17-dione, monohydrochloride.

42. A compound according to claim 38, wherein said compound comprises N-acetyl-5,10-(iminoethano)estrane-3,17-dione.

43. A compound according to claim 39, wherein one of $R_3$ and $R_4$ is hydroxy and the other is hydrogen.

44. A compound according to claim 43, wherein n is 1.

45. A compound according to claim 38 wherein said compound comprises N-acetyl-5,10-(iminoethano)estrane-3β,17β-diol, hemihydrate.

46. A compound according to claim 38, wherein said compound comprises N-ethyl-5,10-(iminoethano)estrane-3β,17β-diol, monochloride.

47. A compound according to claim 38, wherein one of $R_3$ and $R_4$ is hydrogen and the other is acetoxy.

48. A compound according to claim 47, wherein n is 1.

49. A compound according to claim 38, wherein said compound comprises N-ethyl-5,10-(iminoethano)estrane 3β,17β-diol, diacetate monochloride.

* * * * *

UNITED STATES PATENT AND TRADEMARK OFFICE
CERTIFICATE OF CORRECTION

PATENT NO. : 4,495,102

DATED : January 22, 1985

INVENTOR(S) : Leonard N. Nysted

It is certified that error appears in the above-identified patent and that said Letters Patent are hereby corrected as shown below:

Column 3, line 25, formula II, should appear as follows:

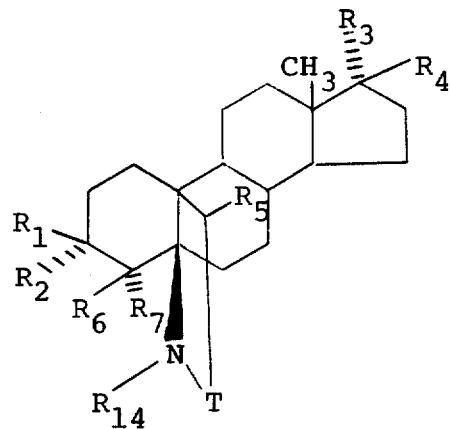

UNITED STATES PATENT AND TRADEMARK OFFICE
CERTIFICATE OF CORRECTION

PATENT NO. : 4,495,102

DATED : January 22, 1985

INVENTOR(S) : Leonard N. Nysted

It is certified that error appears in the above-identified patent and that said Letters Patent are hereby corrected as shown below:

Column 21, formulas XXXIII, XXXIV and XLII, respectively, should appear as follows:

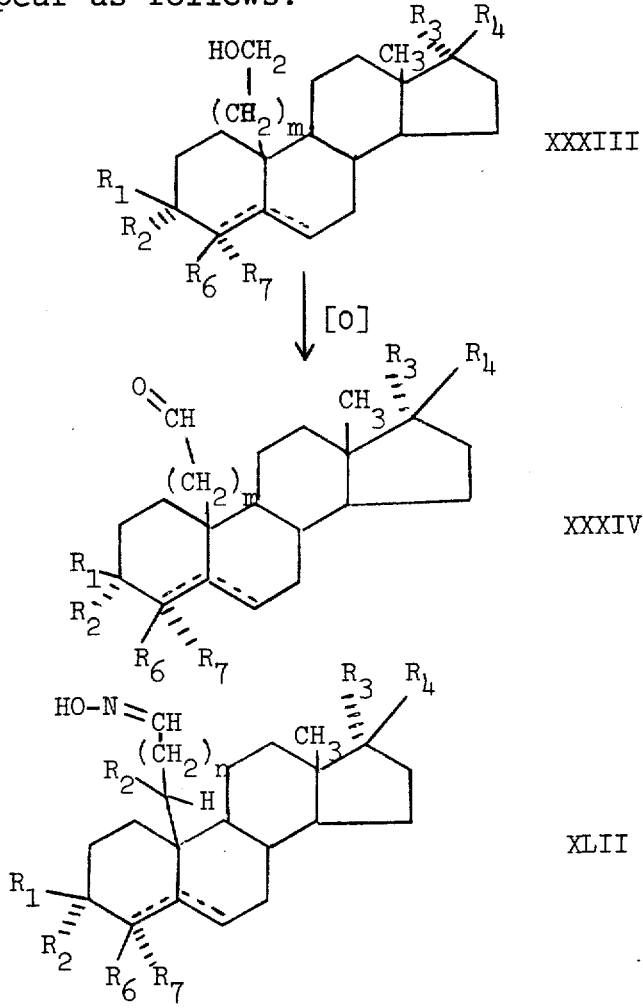

UNITED STATES PATENT OFFICE
CERTIFICATE OF CORRECTION

PATENT NO. : 4,495,102

DATED : January 22, 1985

INVENTOR(S) : Leonard N. Nysted

It is certified that error appears in the above-identified patent and that said Letters Patent are hereby corrected as shown below:

Column 22, formula LIII, that portion of the formula reading

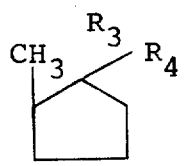     should read     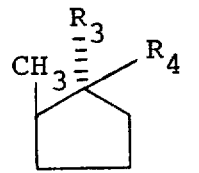 ;

and in formula LIV; and Column 23, formulas LV and LVI that portion of the formula reading

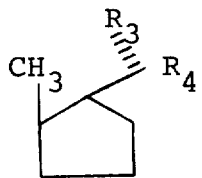     should read     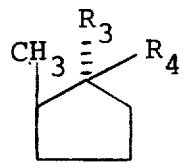

UNITED STATES PATENT AND TRADEMARK OFFICE
CERTIFICATE OF CORRECTION

PATENT NO. : 4,495,102
DATED : January 22, 1985
INVENTOR(S) : Leonard N. Nysted

It is certified that error appears in the above-identified patent and that said Letters Patent are hereby corrected as shown below:

Column 24, formulas should appear as follows:

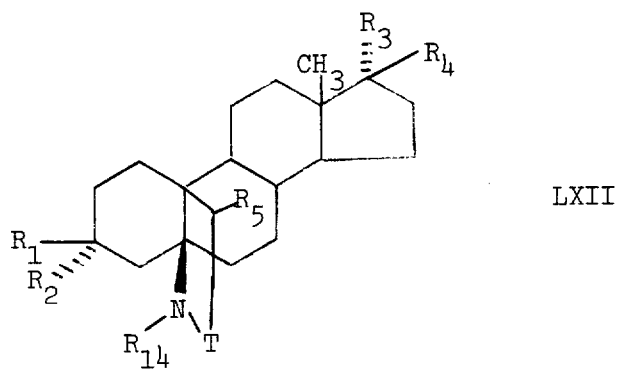

LXII

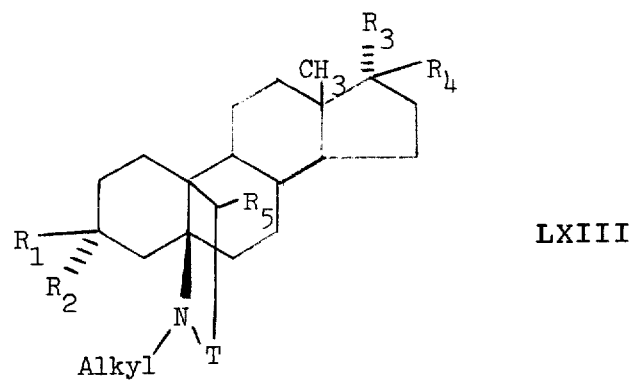

LXIII

UNITED STATES PATENT AND TRADEMARK OFFICE
CERTIFICATE OF CORRECTION

PATENT NO. : 4,495,102
DATED : January 22, 1985
INVENTOR(S) : Leonard N. Nysted

It is certified that error appears in the above-identified patent and that said Letters Patent are hereby corrected as shown below:

Column 24, formulas should appear as follows: (cont.)

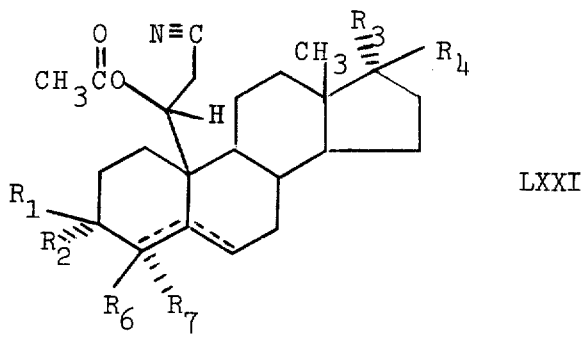

LXXI

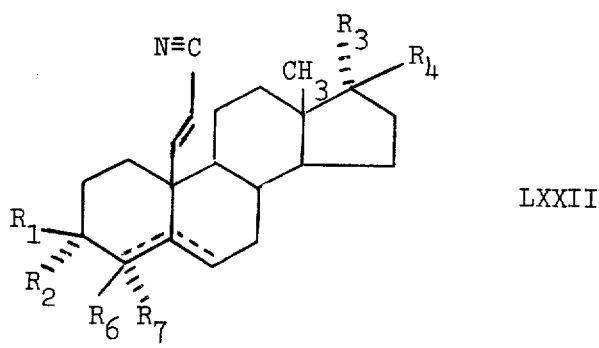

LXXII

UNITED STATES PATENT OFFICE
CERTIFICATE OF CORRECTION

PATENT NO. : 4,495,102

DATED : January 22, 1985

INVENTOR(S) : Leonard N. Nysted

Page 6 of 9

It is certified that error appears in the above-identified patent and that said Letters Patent are hereby corrected as shown below:

Column 25, formulas LXXIII and LXXIV should appear as follows:

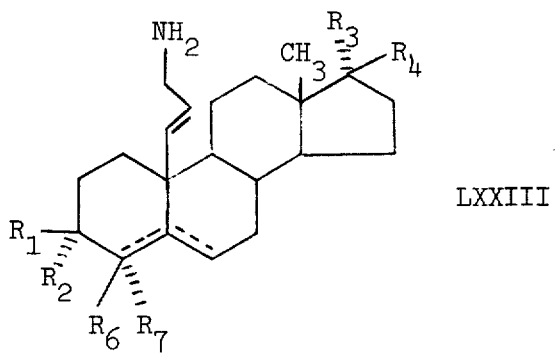

LXXIII

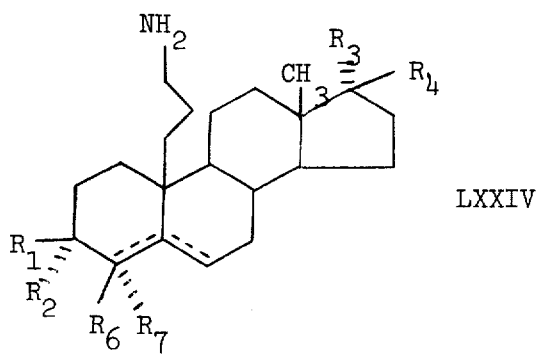

LXXIV

UNITED STATES PATENT OFFICE
CERTIFICATE OF CORRECTION

PATENT NO. : 4,495,102

DATED : January 22, 1985

INVENTOR(S) : Leonard N. Nysted

It is certified that error appears in the above-identified patent and that said Letters Patent are hereby corrected as shown below:

Column 25, Claim 1, line 30, formula I should appear as follows:

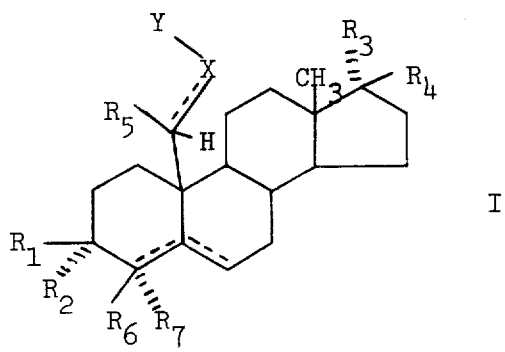

I

Column 26, line 30, following (h), "wherin should read --wherein--.
Column 28, Claim 36, line 65, the formula should appear as follows.

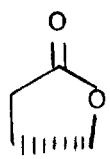

UNITED STATES PATENT AND TRADEMARK OFFICE
CERTIFICATE OF CORRECTION

PATENT NO. : 4,495,102

DATED : January 22, 1985

INVENTOR(S) : Leonard N. Nysted

It is certified that error appears in the above-identified patent and that said Letters Patent is hereby corrected as shown below:

Column 29, Claim 38, formula II, should appear as follows:

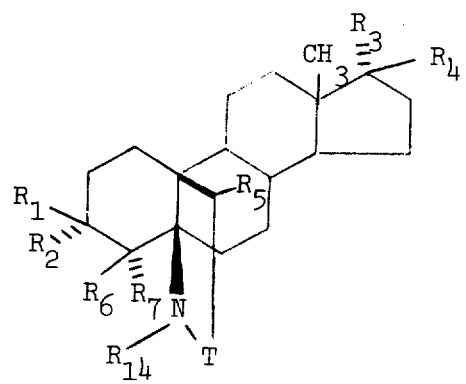

UNITED STATES PATENT AND TRADEMARK OFFICE
CERTIFICATE OF CORRECTION

PATENT NO. : 4,495,102

DATED : January 22, 1985

INVENTOR(S) : Leonard N. Nysted

It is certified that error appears in the above-identified patent and that said Letters Patent is hereby corrected as shown below:

Column 29, Claim 28, line 48, the formula should appear as follows:

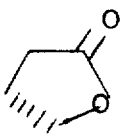

Signed and Sealed this

Eighth Day of October 1985

[SEAL]

Attest:

Attesting Officer

DONALD J. QUIGG

Commissioner of Patents and Trademarks—Designate